US006677156B2

United States Patent
Brough et al.

(10) Patent No.: US 6,677,156 B2
(45) Date of Patent: Jan. 13, 2004

(54) NON-ADENOVIRAL GENE PRODUCT-BASED COMPLEMENTING CELLS FOR ADENOVIRAL VECTORS

(75) Inventors: Douglas E. Brough, Gaithersburg, MD (US); Jason G. D. Gall, Germantown, MD (US); Imre Kovesdi, Rockville, MD (US)

(73) Assignee: GenVec, Inc., Gaithersburg, MD (US)

(*) Notice: Subject to any disclaimer, the term of this patent is extended or adjusted under 35 U.S.C. 154(b) by 0 days.

(21) Appl. No.: 09/911,011

(22) Filed: Jul. 23, 2001

(65) Prior Publication Data

US 2003/0017595 A1 Jan. 23, 2003

(51) Int. Cl.$^7$ .......................... C12N 5/10; C12N 15/63; C12N 15/861
(52) U.S. Cl. .................. 435/456; 435/325; 435/366; 435/367; 435/368; 435/369; 435/370; 435/371; 435/372; 435/373; 435/372.1; 435/372.2; 435/320.1; 435/455; 435/457
(58) Field of Search ................... 435/325, 366, 435/367, 368, 369, 370, 371, 372, 373, 372.1, 372.2, 320.1, 455, 456, 457

(56) References Cited

U.S. PATENT DOCUMENTS 6,127,175 A 10/2000 Vigne et al.

FOREIGN PATENT DOCUMENTS

| FR | 2705686 A | 12/1994 |
|---|---|---|
| WO | WO 01/44280 A | 6/2001 |

OTHER PUBLICATIONS

Brough et al., *J. Virol.*, 70(9), 6497–6501 (Sep. 1996).
Engelhardt et al., *Hum. Gene Ther.*, 5, 1217–1229 (Oct. 1994).
Yang et al., *PNAS USA*, 91, 4407–4411 (May 1994).
Bernards et al., *Virology*, 150 (1), 126–139 (Apr. 15, 1986).
Chiou et al., *J. Virol.*, 68 (10), 6553–6566 (Oct. 1994).
Goldsmith et al., *Virology*, 248 (2), 406–419 (Sep. 1, 1998).
Goodrum et al., *J. Virol.*, 72 (12), 9479–9490 (Dec. 1998).
Harada et al., *J. Virol.*, 73 (7), 5333–5344 (Jul. 1999).
Hay et al., *Hum. Gene Ther.*, 10, 579–590 (Mar. 1, 1999).
Horvath et al., *Virology*, 184 (1), 141–148 (Sep. 1991).
Imperiale et al., *Mol. Cell Biol.*, 4 (5), 867–874 (May 1984).
Kimura et al., *Tumor Res.*, 32, 1–21 (1997).
Kovesdi et al., *Cell*, 45, 219–228 (Apr. 25, 1986).
La Thangue et al., *Cell*, 49, 507–513 (May 22, 1987).
La Thangue et al., *Nucl. Acids Res.*, 18 (10), 2929–2938 (May 25, 1990).
Lee, et al., *Int. J. Cancer*, 88 (3) 454–463 (Nov. 1, 2000).
Rao et al., *PNAS USA*, 89, 7742–7746 (Aug. 1992).
Ries et al., *Nat. Med.*, 6 (10), 1128–1133 (Oct. 2000).
Spector et al., *Virology*, 151 (2), 329–338 (Jun. 1986).
Spergel et al., *PNAS USA*, 88, 6472–6476 (Aug. 1991).
Spergel et al., *J. Virol.*, 66 (2), 1021–1030 (Feb. 1992).
Tevethia et al., *Virology*, 161 (2), 276–285 (Dec. 1987).
Tremblay et al., *Virology*, 144 (1), 35–45 (Jul. 15, 1985).
Wilkinson et al., *Nucl. Acids Res.*, 20 (9), 2233–2239 (May 11, 1992).

*Primary Examiner*—David Guzo
(74) *Attorney, Agent, or Firm*—Leydig, Voit & Mayer, Ltd.

(57) ABSTRACT

The invention provides cells and methods of using the cells for the propagation of replication-deficient adenoviral vectors. The cells comprise at least one heterologous nucleic acid sequence which upon expression produces at least one non-adenoviral gene product that complements in trans for a deficiency in at least one essential gene function of one or more regions of an adenoviral genome so as to propagate a replication-deficient adenoviral vector comprising an adenoviral genome deficient in the at least one essential gene function of the one or more regions when present in the cell.

37 Claims, No Drawings

NON-ADENOVIRAL GENE PRODUCT-BASED COMPLEMENTING CELLS FOR ADENOVIRAL VECTORS

FIELD OF THE INVENTION

This invention pertains to cells for the propagation of adenoviral vectors.

BACKGROUND OF THE INVENTION

Recombinant eukaryotic viral vectors have become a preferred means of gene transfer for many researchers and clinicians. The human adenovirus is one of the most widely used recombinant viral vectors in current gene therapy protocols. As the use of adenoviral vectors becomes more prevalent, the need for systems that efficiently produce adenoviral vectors suitable for administration is increasingly important.

A concern associated with recombinant adenoviral vectors is uncontrolled propagation of the vector upon administration. To address this concern, replication-deficient adenoviral vectors, typically lacking the essential E1 region of the adenoviral genome, have been developed.

The production of replication-deficient adenoviral vectors is commonly accomplished by use of a complementing cell line, such as the 293 cell line developed by Graham et al. (*J. Gen. Virol.*, 36, 59–72 (1977)), which provides in trans the gene functions lacking in the replication-deficient adenoviral vector. A problem associated with many complementing cell lines, including the 293 cell line, is the possibility of homologous recombination between the replication-deficient adenoviral genome and the regions of the adenoviral genome inserted into the complementation cell, resulting in production of replication-competent adenovirus (RCA). To reduce the frequency of RCA formation, several researchers have attempted to construct complementing cell lines comprising viral gene sequences that lack any homology to the adenoviral vector of interest (see, for example, International Patent Applications WO 94/28152 and WO 98/39411, and U.S. Pat. No. 5,994,128 and 6,033,908).

The construction of stable human cell lines that effectively and efficiently complement replication-deficient viral vectors can be difficult. For example, such cell lines often produce significant quantities of E1 and/or E4 gene products, resulting in undesired cytotoxic and/or cytostatic effects. High levels of E1A gene product expression, for example, induce apoptosis in host cells (Rao et al., *PNAS*, 89, 7742–7746 (1992)), while expression of E4 gene products induce p53-independent apoptosis in human cells (Marcellus et al., *J. Virol.*, 72, 7144–53 (1998)). Thus, complementation cells, such as those known in the art, that constitutively express such factors may be associated with poor survival rates prior to and/or during adenoviral vector production.

Animal cells and other viruses encode gene products that are functionally homologous to adenoviral early region genes. Some of these gene products, when transiently expressed in human primary cells or non-human transformed cells, have been shown to complement for deficiencies in E1A gene functions. In particular, Tevethia et al., *Virology*, 161, 276–285 (1987), describes complementation in primary embryonic lung cells of an E1A-deleted adenoviral vector with plasmids encoding immediate early region genes of the human cytomegalovirus (CMV). In addition, the E7 protein of human papilloma virus 16 (HPV16) complements for deficiencies in the E1A region by immortalizing primary rat cells, as shown by co-infection experiments, while tamarin cells transformed by the Epstein-Barr virus (EBV) complement for deficiencies in the E1A and/or E2 regions (see, e.g., Kimura et al., *Tumor Research*, 32, 1–21 (1997), and Horvath et al., *Virology*, 184, 141–148 (1991)). Moreover, some cell lines, including the human hepatoblastoma line HepG2 and certain embryonic stem cell lines, encode factors that provide for the transcriptional transactivation function of the E1A region, as shown by activation of both E2A and/or E1B promoters in the absence of the E1A region (see, e.g., Spergel et al., *Proc. Natl. Acad. Sci. USA*, 88, 6472–6476 (1991), Spergel et al., *J. Virol.*, 66, 1021–1030 (1992), Imperiale et al., *Mol. Cell Biol.*, 4, 867–874 (1984), La Thangue and Rigby, *Cell*, 49, 507–513(1987), and La Thangue et al., *Nuc. Acids Res.*, 18, 2929–2938 (1990)).

Accordingly, there remains a need for alternative cells for propagating replication-deficient adenoviral vectors. The invention provides such cells. These and other advantages of the invention, as well as additional inventive features, will be apparent from the description of the invention provided herein.

BRIEF SUMMARY OF THE INVENTION

The invention provides a cell having a cellular genome comprising a heterologous nucleic acid sequence, which upon expression produces at least one non-adenoviral gene product. The non-adenoviral gene product complements in trans for a deficiency in at least one essential gene function of one or more regions of an adenoviral genome so as to propagate a replication-deficient adenoviral vector comprising an adenoviral genome deficient in the at least one essential gene function of the one or more regions when present in the cell. The invention also provides a transformed human cell comprising a heterologous nucleic acid sequence which upon expression produces at least one non-adenoviral gene product that complements in trans for a deficiency in at least one essential gene function of one or more regions of an adenoviral genome so as to propagate a replication-deficient adenoviral vector comprising an adenoviral genome deficient in the at least one essential gene function of the one or more regions when present in the cell.

The invention also provides a system comprising the inventive cell and a replication-defective adenoviral vector comprising an adenoviral genome deficient in the at least one essential gene function of the one or more regions. The invention further provides a method of propagating a replication-deficient adenoviral vector, wherein the method comprises providing the inventive cell, introducing a replication-deficient adenoviral vector into the inventive cell, and maintaining the cell to propagate the replication-deficient adenoviral vector.

DETAILED DESCRIPTION OF THE INVENTION

The invention provides a cell having a cellular genome comprising at least one heterologous nucleic acid sequence, which upon expression produces at least one non-adenoviral gene product that complements in trans for a deficiency in at least one essential gene function of one or more regions of an adenoviral genome of a replication-deficient adenoviral vector so as to propagate (i.e., replicate the entire life cycle of, or replicate to any stage of the life cycle of) the replication-deficient adenoviral vector when present in the cell.

The cell can be any suitable cell that comprises a genome that can incorporate and preferably retain the heterologous nucleic acid encoding at least one non-adenoviral gene product that complements in trans for a deficiency in at least one essential gene function of one or more regions of an adenoviral genome. The cell desirably can propagate adenoviral vectors and/or adeno-associated viral (AAV) vectors when infected with such vectors or with nucleic acid sequences encoding the adenoviral or AAV genome. Most preferably, the cell can propagate a suitable replication-deficient adenoviral vector upon infection with an appropriate replication-deficient adenoviral vector or transfection with an appropriate replication-deficient viral genome.

Particularly desirable cell types are those that support high levels of adenovirus propagation. The cell preferably produces at least about 10,000 viral particles per cell and/or at least about 3,000 focus forming units (FFU) per cell. More preferably, the cell produces at least about 100,000 viral particles per cell and/or at least about 5,000 FFU per cell. Most preferably, the cell produces at least about 200,000 viral particles per cell and/or at least about 7,000 FFU per cell.

Preferably, the cell is, or is derived from, an anchorage dependent cell, but which has the capacity to grow in suspension cultures. More preferably, the cell is a primary cell. By "primary cell" is meant that the cell does not replicate indefinitely in culture. Examples of suitable primary cells include, but are not limited to, human embryonic kidney (HEK) cells, human retinal cells, and human embryonic retinal (HER) cells. Most preferably, the cells are human embryonic lung (HEL) cells or ARPE-19 cells. Alternatively, the cell can be a transformed cell. The cell is "transformed" in that the cell has the ability to replicate indefinitely in culture. Examples of suitable transformed cells include renal carcinoma cells, CHO cells, KB cells, HEK-293 cells, SW-13 cells, MCF7 cells, and Vero cells. Preferably, the cell is a lung carcinoma cell, such as, for example, a non-small cell lung carcinoma cell. The non-small lung cell carcinoma cell can be a squamous/epidermoid carcinoma cell, an adenocarcinoma cell, or a large cell carcinoma cell. The adenocarcinoma cell can be an alveolar cell carcinoma cell or bronchiolo-alveolar adenocarcinoma cell. Other suitable non-small cell lung carcinoma cells include the cell lines NCI-H2126 (American Type Culture Collection (ATCC) No. CCL-256), NCI-H23 (ATCC No. CRL-5800), NCI-H322 (ATCC No. CRL-5806), NCI-H358 (ATCC No. CRL-5807), NCI-H810 (ATCC No. CRL-5816), NCI-H1155 (ATCC No. CRL-5818), NCI-H647 (ATCC No. CRL-5834), NCI-H650 (ATCC No. CRL-5835), NCI-H1385 (ATCC No. CRL-5867), NCI-H1770 (ATCC No. CRL-5893), NCI-H1915 (ATCC No. CRL-5904), NCI-H520 (HTB-182), and NCI-H596 (ATCC No. HTB-178). Also suitable are squamous/epidermoid carcinoma lines that include HLF-a (ATCC No. CCL-199), NCI-H292 (ATCC No. CRL-1848), NCI-H226 (ATCC No. CRL-5826), Hs 284.Pe (ATCC No. CRL-7228), SK-MES-1 (ATCC No. HTB-58), and SW-900 (ATCC No. HTB-59), large cell carcinoma lines (e.g., NCI-H661 (ATCC No. HTB-183)), and alveolar cell carcinoma lines (e.g., SW-1573 (ATCC No. CRL-2170)). The most preferred cell is selected from the group consisting of an A549 cell (ATCC CCL-185), an NCI-H1299 (ATCC CRL-5803) cell, a Calu-1 cell (ATCC HTB-54), and an NCI-H460 (ATCC HTB-177) cell. Alternatively, the transformed cell need not be a lung carcinoma cell. In this respect, the cell is preferably a HeLa cell (ATCC CCL-2) or an ARPE-19/HPV-16 cell (ATCC CRL-2502). In addition, the transformed cell can be any cell transformed by a viral gene isolated from a non-adenovirus family member, such as, for example, genes encoded by Papillomaviridae, Poxviridae, Polyomaviridae, Hepadnaviridae, Picorniviridae, Flaviviridae, or any other suitable virus family as defined by van Regenmortel et al., eds., *Virus Taxonomy, Seventh Report on the International Committee on Taxonomy of Viruses,* 2000.

The cell comprises at least one heterologous nucleic acid sequence as described herein, i.e., the cell can comprise one heterologous nucleic acid sequence as described herein or more than one heterologous nucleic acid sequence as described herein (i.e., two or more of the heterologous nucleic acid sequences). Such cell lines can be generated in accordance with standard molecular biological techniques as described in International Patent Application WO 95/34671 and U.S. Pat. No. 5,994,106. The heterologous nucleic acid sequence preferably is stably integrated into the nuclear genome of the cell. The heterologous nucleic acid sequence preferably is retained in the cellular genome (and the heterologous nucleic acid sequence, upon expression, preferably produces a non-adenoviral gene product complementing in trans for a deficiency in at least one essential gene function of one or more regions of an adenoviral genome) for at least about 10, more preferably at least about 20, passages in culture (e.g., at least about 30, 40, 100, or more passages). Not to adhere to any particular theory, it is believed that genomic integration of the heterologous nucleic acid sequence encoding the complementing factor is required to generate stable cell lines for adenoviral vector production. Additionally, complementation by transient transfection employs both labor-intensive and inconsistent techniques, resulting in low adenovirus yield and difficulty associated with large-scale viral production. The introduction and stable integration of the heterologous nucleic acid into the genome of the cell requires standard molecular biology techniques that are well within the skill of the art, such as those described in Sambrook et al., *Molecular Cloning, a Laboratory Manual,* 2d ed., Cold Spring Harbor Press, Cold Spring Harbor, N.Y. (1989), Watson et al., *Recombinant DNA,* 2d ed., Scientific American Books (1992), and Ausubel et al., *Current Protocols in Molecular Biology,* Wiley Interscience Publishers, NY (1995).

The "heterologous nucleic acid sequence" can be any nucleic acid sequence that is not obtained from, derived from, or based upon a naturally occurring nucleic acid sequence of the precursor or host cell (i.e., the cell that is modified with the incorporation of the heterologous nucleic acid sequence to form the basis of the inventive cell). By "naturally occurring" is meant that the nucleic acid sequence can be found in nature and has not been synthetically modified. The heterologous nucleic acid sequence also is not obtained from, derived from, or based upon an adenoviral nucleic acid sequence. For example, the heterologous nucleic acid sequence can be a viral, bacterial, plant, or animal nucleic acid sequence. A sequence is "obtained" from a source when it is isolated from that source. A sequence is "derived" from a source when it is isolated from a source but modified in any suitable manner (e.g., by deletion, substitution (mutation), insertion, or other modification to the sequence) so as not to disrupt the normal function of the source gene. A sequence is "based upon" a source when the sequence is a sequence more than about 70% homologous (preferably more than about 80% homologous, more preferably more than about 90% homologous, and most preferably more than about 95% homologous) to the source but obtained through synthetic procedures (e.g., polynucleotide synthesis, directed evolution, etc.). Determining the degree of homology, including the possibility for gaps, can be accomplished using any suitable method (e.g., BLASTnr, provided by GenBank). Notwithstanding the foregoing, the nucleic acid sequence that makes up the heterologous nucleic acid sequence can be naturally found in the host cell, but located at a nonnative position within the cellular genome and/or operably linked to a nonnative promoter.

Any suitable heterologous nucleic acid sequence that encodes a non-adenoviral gene product which complements for a deficiency in an adenoviral essential gene function can be used in the context of the invention. The heterologous nucleic acid sequence desirably is an animal nucleic sequence (e.g., a human or murine nucleic acid sequence, especially such a nucleic acid sequence that encodes a cellular protein) or a viral nucleic acid sequence (e.g., a viral nucleic acid sequence obtained from, derived from, or based upon CMV, EBV, HPV, or herpes simplex virus (HSV)).

The identification of heterologous nucleic acid sequences that encode non-adenoviral gene products which complement for a deficiency in an adenoviral essential gene function is well within the skill of the art. In particular, the ordinarily skilled artisan can cotransfect cells that do not normally express any adenoviral gene products with an expression construct comprising the heterologous nucleic acid sequence and a construct comprising a reporter gene (e.g., chloramphenicol acetyltransferase (CAT)) whose expression is dependent (directly or indirectly) on the presence of an essential adenoviral gene product, e.g., whose expression is regulated by an adenoviral E1A-responsive promoter such as the E1B or E2A promoter (Spergel et al., *J. Virol.*, 66, 1021–1030 (1992)). Expression of the reporter gene, which can be determined by measuring reporter gene activity, indicates that the non-adenoviral gene product produced by the heterologous nucleic acid sequence complements for a deficiency in an adenoviral essential gene function, e.g., the transcription transactivating function of the E1A region. Moreover, the ordinarily skilled artisan can determine whether the non-adenoviral gene product transforms cells through transfection experiments as described by Kimura et al., supra. Other experiments involving only standard molecular biology techniques, such as those described in Sambrook et al., supra, can be performed to determine whether the non-adenoviral gene product complements for a deficiency in other adenoviral essential gene functions.

Examples of suitable heterologous nucleic acid sequences include viral and cellular nucleic acid sequences encoding a non-adenoviral gene product that complements for a deficiency in an adenoviral essential gene function in the E1A region of a replication-deficient adenoviral genome. Preferred heterologous nucleic acid sequences encoding a non-adenoviral gene product that complements for a deficiency in an essential gene function of the E1A region include the immediate early (IE) region genes I and II of human CMV, the E7 gene of HPV 16, and EBV nucleic acid sequences, as well as nucleic acids of the human HepG2 cell line, the mouse F9 teratocarcinoma stem cell line, and the mouse PCC4 teratocarcinoma stem cell line (see, e.g., Spergel et al., Imperiale et al., and La Thangue et al., supra). Other examples of heterologous nucleic acid sequences include viral and cellular nucleic acid sequences encoding a non-adenoviral gene product that complements for a deficiency in an essential gene function in the E1B region of a replication-deficient adenoviral genome. Preferred heterologous nucleic acid sequences encoding a non-adenoviral gene product that complements for a deficiency in an essential gene function of the E1B region, particularly the E1B-19 kD protein and/or the E1B-55 kD protein, include nucleic acid sequences encoding the Bcl-2 protein (see, e.g., Rao et al., supra). Moreover, certain cells contain nucleic acid sequences that endogenously complement for adenoviral E1B essential gene function deficiencies, and the heterologous nucleic acid sequences can be those cellular nucleic acid sequences that provide such complementation, including HEK cells (see, e.g., Bernards et al., *Virology*, 150, 126–139 (1986)), A549 cells (ATCC No. CCL-185), IMR90 fibroblast cells (ATCC No. CCL-186) (see, e.g., Hay et al., *Human Gene Ther.*, 10, 579–590 (1999)), H460 cells (ATCC No. HTB-177) (see, e.g., Lee et al., *Int. J. Cancer*, 88, 454–463 (2000)), and HCT116 cells (ATCC No. HCL-247) (see, e.g., Ries et al., *Nature Medicine*, 6, 1128–1133 (2000)). Moreover, a heterologous nucleic acid sequence encoding a non-adenoviral gene product that complements for a deficiency in an adenoviral essential gene function in the E1B-55 kD protein can be used to complement the overlapping functions of the E4-ORF6 protein (see, e.g., Goodrum et al., *J. Virology*, 72, 9479–9490 (1998)). Further examples of heterologous nucleic acid sequences include viral and cellular nucleic acid sequences encoding a non-adenoviral gene product that complements for a deficiency in an essential gene function of the E4 region of a replication-deficient adenoviral genome. Preferred heterologous nucleic acid sequences encoding a non-adenoviral gene product that complements for a deficiency in an essential gene function of the E4 region include nucleic acid sequences encoded by CMV. In particular, the non-adenoviral gene product can complement for a deficiency in an essential gene function of the E4 region that is not shared by an essential gene function of the E1B region.

The heterologous nucleic acid sequence, however, is not limited to these exemplary sequences. Indeed, genetic sequences can vary between different animal and viral species and strains, and this natural scope of allelic variation is included within the scope of the invention. Once a candidate heterologous nucleic acid sequence (e.g., a CMV IE1 and/or IE2 gene region) is identified, other heterologous nucleic acid sequences encoding a non-adenoviral gene product with similar activity can be obtained by searching the myriad of available genetic sequence databases that enable DNA sequence searching based on homology. One such database is the GenBank sequence database provided by the National Center for Biotechnology Information (NCBI). Preferably, the heterologous sequence comprises a nucleic acid sequence which exhibits at least about 75%, desirably at least about 85%, and more preferably at least about 95%, nucleic acid sequence identity to (e.g., at least 97% identity to, or 100% identity with) any of the heterologous nucleic acids described herein. Determining the degree of homology, including the possibility for gaps, can be accomplished using any suitable method (e.g., BLASTnr, provided by GenBank).

In addition to searching sequence databases, a candidate heterologous nucleic acid sequence encoding a non-adenoviral gene product can be used as a probe to identify homologous sequences from a genetic library via hybridization. An appropriate homologous sequence encodes a non-adenoviral gene product that functions similarly, if not identically, to the non-adenoviral gene product encoded by the candidate heterologous nucleic acid sequence. A suitable heterologous nucleic acid sequence is that which hybridizes to a reference nucleic acid sequence (e.g., a CMV IE1 and/or IE2 gene region) under at least moderate, preferably high, stringency conditions. Exemplary moderate stringency conditions include overnight incubation at 37° C. in a solution comprising 20% formamide, 5×SSC (150 mM NaCl and 15 mM trisodium citrate), 50 mM sodium phosphate (pH 7.6), 5×Denhardt's solution, 10% dextran sulfate, and 20 mg/ml denatured sheared salmon sperm DNA, followed by washing in 1×SSC at about 37–50° C., or substantially similar conditions, e.g., the moderately stringent conditions described in Sambrook et al., supra. High stringency conditions are conditions that, for example (1) use low ionic strength and high temperature for washing, such as with a composition comprising 0.015 M sodium chloride and 0.0015 M sodium citrate, and 0.1% sodium dodecyl sulfate (SDS) at 50° C., (2) employ a denaturing agent during hybridization, such as a composition comprising formamide, for example, 50% (v/v) formamide with 0.1% bovine serum albumin (BSA), 0.1% Ficoll, 0.1% polyvinylpyrrolidone (PVP), and 50 mM sodium phosphate buffer at pH 6.5 with 750 mM sodium chloride and 75 mM sodium citrate at 42° C., or (3) employ a composition comprising 50% formamide, 5×SSC (0.75 M NaCl and 0.075 M sodium citrate), 50 mM sodium phosphate (pH 6.8), 0.1% sodium pyrophosphate, 5×Denhardt's solution, and sonicated salmon sperm DNA (50 μg/ml), 0.1% SDS, and 10% dextran sulfate at 42° C., with washes at (i) 42° C. in 0.2×SSC, (ii) at 55° C. in 50% formamide, and (iii) at 55° C. in 0.1×SSC (preferably in combination with EDTA). Additional details and explanation of stringency of hybridization reactions are provided in, e.g., Ausubel et al., supra.

Moreover, the heterologous nucleic acid sequence can include one or more mutations (e.g., point mutations, deletions, insertions, etc.) from a corresponding naturally occurring heterologous nucleic acid sequence. Thus, where mutations are introduced in the nucleic acid sequence to effect one or more amino acid substitutions in an encoded non-adenoviral gene product, such mutations desirably effect such amino acid substitutions whereby codons encoding positively-charged residues (H, K, and R) are substituted with codons encoding positively-charged residues, codons encoding negatively-charged residues (D and E) are substituted with codons encoding negatively-charged residues, codons encoding neutral polar residues (C, G, N, Q, S, T, and Y) are substituted with codons encoding neutral polar residues, and codons encoding neutral non-polar residues (A, F, I, L, M, P, V, and W) are substituted with codons encoding neutral non-polar residues. Such mutations can also be introduced to effect one or more amino acid substitutions in the N- or C-terminus of the encoded non-adenoviral gene product.

The heterologous nucleic acid sequence can be any suitable nucleic acid sequence as described herein that, upon expression, produces one or more gene products that complement for one or more deficiencies in any adenoviral essential gene functions (i.e., functions necessary for adenovirus propagation). By "complements for a deficiency in an essential gene function of an adenoviral genome" is meant that the gene product encoded by the heterologous nucleic acid sequence exhibits an adenoviral gene function that is essential (i.e., necessary) for an adenoviral vector to propagate in a cell. For example, the non-adenoviral gene product can induce transcription of promoters regulated by the E1A protein, such as the E2A promoter.

The non-adenoviral gene product can be an RNA sequence or a protein (e.g., a peptide or a polypeptide). Preferably, the non-adenoviral gene product is a protein. By "non-adenoviral gene product" is meant that the gene product exhibits less than about 50% (preferably less than about 30%, more preferably less than about 10%, and most preferably less than about 1%) homology to a gene product encoded by an adenovirus (preferably an adenovirus of serotype 2 or 5). The degree of homology can be determined using any suitable method known in the art (e.g., BLAST programs).

The heterologous nucleic acid preferably encodes a full-length non-adenoviral gene product, especially a non-adenoviral protein. Alternatively, the heterologous nucleic acid encodes a functional portion of a non-adenoviral gene product, especially a protein. A "functional portion" is any portion of a non-adenoviral gene product that complements for a deficiency in an adenoviral essential gene function at a measurable level. A functional portion of a non-adenoviral gene product can be identified using any suitable method known in the art, such as the transfection experiments described herein.

The heterologous nucleic acid sequence, upon expression, produces at least one non-adenoviral gene product that provides an adenoviral essential gene function, i.e., that complements in trans for one or more deficiencies in any adenoviral essential gene function (i.e., a function that is necessary for adenovirus propagation). The heterologous nucleic acid sequence, upon expression, can produce a non-adenoviral gene product that complements for two or more deficiencies in adenoviral essential gene functions (from the same or different regions of the adenoviral genome). The heterologous nucleic acid sequence, upon expression, can produce two or more non-adenoviral gene products, each of which complements for a deficiency (i.e., at least one deficiency, including but not limited to, two or more deficiencies) in adenoviral essential gene functions (from the same or different regions of the adenoviral genome).

Essential adenoviral gene functions are those gene functions that are required for propagation (i.e., replication) of a replication-deficient adenoviral vector. Essential gene functions are encoded by, for example, the adenoviral early regions (e.g., the E1, E2, and E4 regions), late regions (e.g., the L1–L5 regions), genes involved in viral packaging (e.g., the IVa2 gene), and viral-associated RNAs (e.g., VA-RNA I and/or VA-RNA II). Thus, the non-adenoviral gene product complements for a deficiency in at least one adenoviral essential gene function encoded by the early regions, late regions, viral packaging regions, viral-associated RNA regions, or combinations thereof, including all adenoviral functions (e.g., to enable propagation of adenoviral amplicons comprising only inverted terminal repeats (ITRs) and the packaging signal or only ITRs and an adenoviral promoter).

The non-adenoviral gene product desirably complements for a deficiency in at least one essential gene function of one or more regions of the adenoviral genome selected from the early regions, e.g., the E1, E2, and E4 regions. Preferably, the non-adenoviral gene product complements in trans for a deficiency in at least one essential gene function of the E1 region of the adenoviral genome. More preferably, the non-adenoviral gene product complements in trans for a deficiency in at least one essential gene function of an adenoviral E1A coding sequence and/or an adenoviral E1B coding sequence (which together comprise the E1 region). In that respect, one non-adenoviral gene product can complement in trans for a deficiency in at least one essential gene function of the E1A coding sequence and another (i.e., different) non-adenoviral gene product can complement in trans for a deficiency in at least one essential gene function of the E1B coding sequence. In addition or alternatively to the non-adenoviral gene product(s) complementing in trans for the aforementioned deficiencies in adenoviral essential gene functions, the same or different non-adenoviral gene product(s) can complement for a deficiency in at least one essential gene function of the E2(particularly the adenoviral DNA polymerase and terminal protein) and/or E4 regions of the adenoviral genome. Desirably, a cell that complements for a deficiency in the E4 region comprises the E4-ORF6 gene sequence and produces the E4-ORF6 protein. Such a cell desirably comprises at least ORF6 and no other ORF of the E4 region of the adenoviral genome.

Although primary cells are acceptable for use as complementing cell lines, the invention further provides a transformed human cell comprising a heterologous nucleic acid sequence, which upon expression produces at least one non-adenoviral gene product that complements in trans for a deficiency in at least one essential gene function of one or more regions of an adenoviral genome so as to propagate a replication-deficient adenoviral vector comprising an adenoviral genome deficient in the at least one essential gene function of the one or more regions when present in the cell.

The cell is "transformed" in that the cell has the ability to replicate indefinitely in culture. The human transformed cells are advantageous over primary cells for generating complementing cell lines in some respects. In particular, transformation of primary cells with the E1 transcription unit may result in an E1 expression pattern that is optimal for transformation, but not complementation. Moreover, expression of the non-adenoviral gene product may be sufficient for complementation, but not transformation. In contrast, the use of transformed cells eliminates any uncertainty related to the transforming ability of a given gene product, and allows the skilled artisan to directly determine complementation by the non-adenoviral gene product.

The transformed human cell can be any suitable such cell that comprises a genome capable of incorporating and preferably retaining the heterologous nucleic acid encoding at least one non-adenoviral gene product that complements in trans for a deficiency in at least one adenoviral essential gene function. Preferably, the cell can produce adenoviral vectors and/or adeno-associated viral (AAV) vectors when infected with such vectors or with nucleic acid sequences encoding the adenoviral genome. Most preferably, the cell can produce a replication-deficient adenoviral vector upon infection with the virus or transfection with the viral genome. Particularly desirable cell types are those that support high levels of adenovirus propagation, with desired viral particles per cell and/or focus forming units per cell values as described herein with respect to the inventive cell with a cellular genome comprising the heterologous nucleic acid sequence.

Preferably, the cells are, or are derived from, anchorage dependent cells, but which have the capacity to grow in suspension cultures. Examples of suitable human transformed cells include HEK-293 cells, SW-13 cells, MCF7 cells, and lung carcinoma cells such as those described herein with respect to the inventive cell with a cellular genome comprising the heterologous nucleic acid sequence. Most preferably, the cell is selected from the group consisting of an A549 cell, an NCI-H1299 cell, a Calu-1 cell, and an NCI-H460 cell. Alternatively, the cell need not be a lung carcinoma. In this respect the cell is preferably a HeLa cell or an ARPE-16/HPV-16 cell. In addition, the human transformed cell can be any human cell transformed by a viral gene isolated from a non-adenovirus family member, such as, for example, genes encoded by Papillomaviridae, Poxviridae, Polyomaviridae, Hepadnaviridae, Picorniviridae, Flaviviridae, or any other suitable virus family as defined by van Regenmortel et al., eds., *Virus Taxonomy, Seventh Report on the International Committee on Taxonomy of Viruses,* 2000. The cell, however, is not limited to these specific examples. Indeed, the cell can be derived from, obtained from, or based upon any suitable human transformed cell.

The human transformed cell can comprise one heterologous nucleic acid sequence as described herein or more than one heterologous nucleic acid sequence as described herein (i.e., two or more of the heterologous nucleic acid sequence). The heterologous nucleic acid sequence can be integrated into the cellular genome or can be otherwise present in the cell. Desirably, the heterologous nucleic acid sequence is integrated into the cellular genome as described herein with respect to the inventive cell with a cellular genome comprising the heterologous nucleic acid sequence. When the heterologous nucleic acid sequence is not integrated into the cellular genome, the heterologous nucleic acid sequence can reside, for example, on a plasmid, liposome, or any other type of molecule that can harbor a heterologous nucleic acid sequence extrachromosomally. The transformed human cell can comprise one or more heterologous nucleic acid sequences in the cellular genome and one or more heterologous nucleic acid sequences that are not incorporated into the cellular genome. The descriptions of the heterologous nucleic acid sequence, non-adenoviral gene product, and complementation of deficiencies in adenoviral essential gene functions as described herein with respect to the inventive cell with a cellular genome comprising the heterologous nucleic acid sequence also apply to those same features of the human transformed cell.

Although not preferred, a helper virus can be provided to the inventive cell with a cellular genome comprising the heterologous nucleic acid sequence or the inventive human transformed cell in the event that either cell does not complement for all deficiencies in essential gene functions of the adenoviral genome of the adenoviral vector to be propagated. The helper virus contains coding sequences that, upon expression, produce gene products which provide in trans those gene functions that are necessary for adenoviral propagation (e.g., the IVa2 gene function). In other words, the helper virus can comprise any adenoviral nucleic acid sequence that is not required in cis (e.g., the ITRs and packaging signal) for propagation.

Both the inventive cell with a cellular genome comprising the heterologous nucleic acid sequence and the inventive human transformed cell can further comprise an "enhancing" heterologous nucleic acid sequence which upon expression produces at least one non-adenoviral gene product that enhances propagation of a replication-deficient adenoviral vector without necessarily complementing for a deficiency in an adenoviral essential gene function, so as to propagate more replication-deficient adenoviral vectors when present in the cell than when the "enhancing" heterologous nucleic acid sequence is absent from the cell. Although genomic integration of this "enhancing" heterologous nucleic acid sequence is preferred, the "enhancing" heterologous nucleic acid sequence also can be maintained in the cell extrachromosomally (e.g., on a plasmid).

The "enhancing" heterologous nucleic acid sequence can encode, for example, a protein that inhibits and/or prevents apoptosis (e.g., Bcl-2). Moreover, the "enhancing" heterologous nucleic acid sequence can encode, for example, an RNA molecule or protein that improves the efficiency or rate of replication-deficient adenoviral vector propagation.

The expression of any of the heterologous nucleic acid sequences in the inventive cell with a cellular genome comprising the heterologous nucleic acid sequence or the inventive transformed human cell is controlled by a suitable expression control sequence operably linked to the heterologous nucleic acid sequence. An "expression control sequence" is any nucleic acid sequence that promotes, enhances, or controls expression (typically and preferably transcription) of another nucleic acid sequence. Suitable expression control sequences include constitutive promoters, inducible promoters, repressible promoters, and enhancers. The heterologous nucleic acid sequence can be regulated by its endogenous promoter or by a non-native promoter sequence. Examples of suitable non-native promoters include the CMV immediate early promoter, the phosphoglycerate kinase (PGK) promoter, the long terminal repeat promoter of the Rous sarcoma virus (LTR-RSV), the sheep metallothionien promoter, and the human ubiquitin C promoter. Alternatively, expression of the heterologous nucleic acid sequence can be controlled by a chimeric promoter sequence. The promoter sequence is "chimeric" when it comprises at least two nucleic acid sequence portions obtained from, derived from, or based upon at least two different sources (e.g., two different regions of an organism's genome, two different organisms, or an organism combined with a synthetic sequence). In addition, the expression control sequence can be activated upon infection with a viral vector, such as a replication-deficient adenoviral vector, or contact with viral peptides. When the nucleic acid sequence that makes up the heterologous nucleic acid sequence is naturally found in the host cell but operably linked to a nonnative promoter, the nonnative promoter can be introduced into the inventive cell by homologous recombination (see, e.g., U.S. Pat. No. 5,641,670) or by random promoter insertion (see, e.g., Harrington et al., *Nature Biotechnology*, 19, 440–445 (2001)). Suitable expression control sequences can be determined using eukaryotic expression systems such as are generally described in Sambrook et al., supra, and by using reporter gene systems (see, e.g., Taira et al., *Gene*, 263, 285–292 (2001)).

The invention also provides a system comprising the inventive cell and a replication-deficient adenoviral vector comprising an adenoviral genome deficient in the at least one essential gene function of the one or more regions (i.e., a replication-deficient adenoviral vector comprising the deficiencies complemented for by the inventive cell). The invention further provides a method of propagating a replication-deficient adenoviral vector. The method comprises providing a cell of the invention, introducing the replication-deficient adenoviral vector into the cell, wherein the replication-deficient adenoviral vector comprises an adenoviral genome deficient in the at least one essential gene function of the one or more regions, and maintaining the cell (e.g., under conditions suitable for adenoviral propagation) to propagate the adenoviral vector.

The adenoviral vector is deficient in at least one gene function (of the adenoviral genome) required for viral propagation (i.e., an adenoviral essential gene function), thereby resulting in a "replication-deficient" adenoviral vector. The adenoviral vector is deficient in the one or more adenoviral essential gene functions complemented for by the inventive cell to allow for propagation of the replication-deficient adenoviral vector when present in the cell.

Preferably, the adenoviral vector is deficient in at least one essential gene function of the E1 region, e.g., the E1a region and/or the E1b region, of the adenoviral genome that is required for viral replication. The recombinant adenovirus also can have a mutation in the major late promoter (MLP), as discussed in International Patent Application WO 00/00628. More preferably, the vector is deficient in at least one essential gene function of the E1 region and at least part of the nonessential E3 region (e.g., an Xba I deletion of the E3 region). The adenoviral vector can be "multiply deficient," meaning that the adenoviral vector is deficient in one or more essential gene functions in each of two or more regions of the adenoviral geonome. For example, the aforementioned E1-deficient or E1-, E3-deficient adenoviral vectors can be further deficient in at least one essential gene of the E4 region and/or at least one essential gene of the E2 region (e.g., the E2A region and/or E2B region). Adenoviral vectors deleted of the entire E4 region can elicit lower host immune responses. Examples of suitable adenoviral vectors include adenoviral vectors that lack (a) all or part of the E1 region and all or part of the E2 region, (b) all or part of the E1 region, all or part of the E2 region, and all or part of the E3 region, (c) all or part of the E1 region, all or part of the E2 region, all or part of the E3 region, and all or part of the E4 region, (d) at least part of the E1a region, at least part of the E1b region, at least part of the E2a region, and at least part of the E3 region, (e) at least part of the E1 region, at least part of the E3 region, and at least part of the E4 region, and (f) all essential adenoviral gene products (e.g., adenoviral amplicons comprising ITRs and the packaging signal only). The adenoviral vector can contain a wild type pIX gene. Alternatively, although not preferably, the adenoviral vector also can contain a pIX gene that has been modified by mutation, deletion, or any suitable DNA modification procedure.

The replication-deficient adenoviral vector can be generated by using any species, strain, subtype, or mixture of species, strains, or subtypes, of an adenovirus or a chimeric adenovirus as the source of vector DNA. The adenoviral vector can be any adenoviral vector capable of growth in a cell, which is in some significant part (although not necessarily substantially) derived from or based upon the genome of an adenovirus. The adenoviral vector preferably comprises an adenoviral genome of a wild-type adenovirus of group C, especially of serotype (i.e., Ad5). Adenoviral vectors are well known in the art and are described in, for example, U.S. Pat. Nos. 5,559,099, 5,712,136, 5,731,190, 5,837,511, 5,846,782, 5,851,806, 5,962,311, 5,965,541, 5,981,225, 5,994,106, 6,020,191, and 6,113,913, International Patent Applications WO 95/34671, WO 97/21826, and WO 00/00628, and Thomas Shenk, "Adenoviridae and their Replication," and M. S. Horwitz, "Adenoviruses," Chapters 67 and 68, respectively, in *Virology*, B. N. Fields et al., eds., 3d ed., Raven Press, Ltd., New York (1996).

The construction of adenoviral vectors is well understood in the art and involves the use of standard molecular biological techniques, such as those described in, for example, Sambrook et al., supra, Watson et al., supra, Ausubel et al., supra, and other references mentioned herein. Moreover, adenoviral vectors can be constructed and/or purified using the methods set forth, for example, in U.S. Pat. No. 5,965,358 and International Patent Applications WO 98/56937, WO 99/15686, and WO 99/54441.

When the cell is used to propagate a replication-deficient adenoviral vector, it is desirable to avoid a recombination event between the cellular genome (of the cell) and the adenoviral genome (of the adenoviral vector) that would result in the generation of a replication-competent adenovirus (RCA). As such, there is preferably insufficient overlap between the genome of the cell and the replication-deficient adenoviral vector genome to mediate a recombination event sufficient to result in a replication-competent adenovirus. If overlap exists, the overlapping sequences desirably are predominantly located in the nucleic acid flanking the coding region of the complementation factor (the "trans-complementing region") in the cellular genome and the nucleotide sequences adjacent to the missing region(s) of the adenoviral genome. Ideally, there is no overlap between the cellular genome and the adenoviral vector genome. However, it is acceptable that partial overlap exists between the cellular genome and the adenoviral vector genome on one side of the trans-complementing region. In such an event, the region of homology preferably is contiguous with the trans-complementing region. For example, when the cell comprises a trans-complementing region comprising a nucleotide sequence of the adenoviral E1 region, the cell desirably lacks homologous sequences on the 5'side (left side) of the trans-complementing region corresponding to the adenoviral inverted terminal repeats (ITRs) and packaging signal sequences, but contains homologous sequences on the 3'side (right side) of the trans-complementing region. The region of homology is at least about 2000 base pairs, preferably at least about 1000 base pairs (e.g., at least about 1500 base pairs), more preferably at least about 700 base pairs, and most preferably at least about 300 base pairs. The generation of RCA desirably is diminished such that (a) the cell produces less than about one replication-competent adenoviral vector for at least about 20 passages after infection with the adenoviral vector, (b) the cell produces less than about one replication-competent adenoviral vector in a period of about 36 hours post-infection, (c) the cell produces less than about one replication-competent adenoviral vector per $1 \times 10^{10}$ total viral particles (preferably $1 \times 10^{11}$ total viral particles, more preferably $1 \times 10^{12}$ total viral particles, and most preferably $1 \times 10^{13}$ total viral particles), or any combination of (a)–(c). Optimally, the amount of overlap between the cellular genome and the adenoviral genome (i.e., the genome of the adenoviral vector being propagated in the cell) is insufficient to mediate a homologous recombination event that results in a replication-competent adenoviral vector such that replication-competent adenoviruses are eliminated from the vector stocks resulting from propagation of the replication-deficient adenoviral vector in the cell. Virus growth yield and virus plaque formation have been previously described (see, e.g., Burlseson et al., *Virology: a Laboratory Manual,* Academic Press Inc. (1992)), and measuring RCA as a function of plaque forming units is described in U.S. Pat. 5,994,106.

The following examples further illustrate the invention but, of course, should not be construed as in any way limiting its scope.

EXAMPLE 1

This example describes the construction of a primary cell having a cellular genome comprising the CMV immediate early gene regions 1 and 2 heterologous nucleic acid sequences, which, upon expression, produce at least one non-adenoviral protein (i.e., the IE1 and IE2 proteins).

Plasmid pCMVXbaEpuro contains the XbaI-E fragment of HCMV DNA (0.68–0.77 map units), which includes the CMV immediate early (IE) regions 1 and 2 inserted into the NruI-ApaI digested pSMTpuro-ORF6 plasmid. The pSMTpuro-ORF6 plasmid contains the adenovirus 5 E4-ORF6 gene under the control of the sheep metallothionein promoter (see, e.g., International Patent Application WO 95/34671).

Primary human embryonic lung (HEL) cells are cultured in Dulbecco's modified Eagle's medium (DMEM) supplemented with 10% calf serum, 100 µg of penicillin per milliliter (all components from Life Technologies, Gaithersburg, Md.). The HEL cells are then transfected with pCMVXbaEpuro by the calcium phosphate method (Sambrook et al., supra). Following transfection, 2.5 µg/ml of puromycin is added to the culture medium for selection of the CMV IE1 and IE2 expressing cells, which are clonally isolated and propagated (see Sambrook et al., supra). Approximately 24 hours post-transfection, expression of CMV IE1 and IE2 genes is assayed via Northern and Western blotting. Integration of the CMV sequences is confirmed by Southern blotting.

EXAMPLE 2

This example describes a method for demonstrating the ability of an inventive cell having a cellular genome comprising a heterologous nucleic acid sequence encoding the CMV IE1 and IE2 proteins to support propagation and production of a replication-deficient adenoviral vector.

The HEL cells of Example 1 are cultured using routine tissue culture techniques. Monolayers at passages 5 and 10 are screened for E1A complementation by a virus production assay (see, e.g., Burlseson et al., *Virology: A Laboratory Manual,* Academic Press Inc. (1992)). In that respect, the cells are infected with a replication-deficient adenoviral vector wherein the E1A region has been deleted from the adenoviral genome thereof. Specifically, the cells are infected with an E1A-deficient adenoviral vector, which contains the E1B region encoding the protein AdE 1B, at a multiplicity of infection (MOI) of 10. Cell lysates are prepared at 3 days post-infection (d.p.i.), and the amount of active virus in the lysates is determined by a focal forming unit (FFU) assay (Cleghorn et al., *Virology,* 197, 564–575 (1993)). The detection of significant yields of AdE1B for the cells at passages 5 and 10 evidences the ability of the cells to complement in trans for deficiencies in adenoviral essential gene functions of the E1A region of the adenoviral genome.

EXAMPLE 3

This example describes the construction of a transformed human cell having a cellular genome comprising the CMV immediate early gene regions 1 and 2 heterologous nucleic acid sequences, which, upon expression, produce at least one non-adenoviral protein (i.e., the IE1 and IE2 proteins).

HeLa cells (ATCC CCL-2) are cultured in Dulbecco's modified Eagle's medium (DMEM) supplemented with 10% calf serum, 100 µg of penicillin per milliliter (all components from Life Technologies, Gaithersburg, Md.). The HeLa cells are then transfected with the pCMVXbaEpuro plasmid of Example 1 by the calcium phosphate method (Sambrook et al., supra). Following transfection, 2.5 µg/ml of puromycin is added to the culture medium for selection of the CMV IE1 and IE2 expressing cells, which are clonally isolated and propagated (see Sambrook et al., supra). Approximately 24 hours post-transfection, expression of CMV IE1 and IE2 genes is assayed via Northern and Western blotting. Integration of the CMV sequences is confirmed by Southern blotting.

EXAMPLE 4

This example describes a method for demonstrating the ability of an inventive cell having a cellular genome comprising a heterologous nucleic acid sequence encoding the CMV IE1 and IE2 proteins to support propagation and production of a replication-deficient adenoviral vector.

The HeLa cells of Example 3 are cultured using routine tissue culture techniques. Monolayers at passages 5 and 10 are screened for E1A complementation by a virus production assay (see, e.g., Burlseson et al., *Virology: A Laboratory Manual*, Academic Press Inc. (1992)). In that respect, the cells are infected with a replication-deficient adenoviral vector wherein the E1A region has been deleted from the adenoviral genome thereof. Specifically, the cells are infected with an E1A-deficient adenoviral vector, which contains the E1B region encoding the protein AdE1B, at a multiplicity of infection (MOI) of 10. Cell lysates are prepared at 3 days post-infection (d.p.i.), and the amount of active virus in the lysates is determined by a focal forming unit (FFU) assay (Cleghom et al., *Virology*, 197, 564–575 (1993)). The detection of significant yields of AdE1B for the cells at passages 5 and 10 evidences the ability of the cells to complement in trans for deficiencies in adenoviral essential gene functions of the E1A region of the adenoviral genome.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A human retinal cell comprising at least one heterologous nucleic acid sequence which upon expression produces at least one non-adenoviral gene product that complements in trans for a deficiency in at least one essential gene function of one or more regions of an adenoviral genome selected from the group consisting of the E1, E2A, and E4 regions so as to propagate a replication-deficient adenoviral vector comprising an adenoviral genome deficient in the at least one essential gene function of the E1, E2A, and/or E4 regions when present in the human retinal cell.

2. The human retinal cell of claim 1, wherein at least one non-adeno viral gene product complements in trans for a deficiency in the E1A region of an adenoviral genome.

3. The human retinal cell of claim 1, wherein at least one non-adenoviral gene product complements in trans for a deficiency in E4-ORF6 of an adenoviral genome.

4. The human retinal cell of claim 1, wherein at least one non-adenoviral gene product is a viral protein.

5. The human retinal cell of claim 1, wherein at least one non-adenoviral gene product is a cellular protein.

6. The human retinal cell of claim 1, wherein the human retinal cell further comprises a heterologous nucleic acid sequence which upon expression produces a non-adenoviral gene product that enhances propagation of the replication-deficient adenoviral vector, so as to produce more replication-deficient adenoviral vectors when the heterologous nucleic acid sequence is present in the human retinal cell than when it is absent from the human retinal cell.

7. A method of propagating a replication-deficient adenoviral vector, which method comprises:
   (a) providing the human retinal cell of claim 1,
   (b) introducing a replication-deficient adenoviral vector into the human retinal cell, wherein the replication-deficient adenoviral vector comprises an adenoviral genome deficient in the at least one essential gene function of the E1, E2A, and/or E4 regions, and
   (c) maintaining the human retinal cell to propagate the replication-deficient adenoviral vector.

8. The human retinal cell of claim 1, wherein the human retinal cell is a human embryonic retinal cell.

9. The human retinal cell of claim 1, wherein the at least one heterologous nucleic acid sequence is integrated into the cellular genome.

10. The method of claim 7, wherein at least one non-adenoviral gene product complements in trans for a deficiency in the E1A region of an adenoviral genome.

11. The method of claim 7, wherein at least one non-adenoviral gene product complements in trans for a deficiency in E4-ORF6 of an adenoviral genome.

12. The method of claim 7, wherein at least one non-adenoviral gene product is a viral protein.

13. The method of claim 7, wherein at least one non-adenoviral gene product is a cellular protein.

14. The method of claim 7, wherein the human retinal cell is a human embryonic retinal cell.

15. The method of claim 7, wherein the at least one heterologous nucleic acid sequence is integrated into the cellular genome.

16. A lung carcinoma cell comprising at least one heterologous nucleic acid sequence which upon expression produces at least one non-adenoviral gene product that complements in trans for a deficiency in at least one essential gene function of the E1 region of an adenoviral genome and a deficiency in one or more essential gene functions in either or both of the E2A region and the E4 region the adenoviral genome so as to propagate a replication-deficient adenoviral vector comprising an adenoviral genome deficient in the at least one essential gene function of the E1 region and either or both of the E2A region and the E4 region when present in the lung carcinoma cell.

17. The lung carcinoma cell of claim 16, wherein at least one non-adenoviral gene product complements in trans for a deficiency in the E1A region of an adenoviral genome.

18. The lung carcinoma cell of claim 16, wherein at least one non-adenoviral gene product complements in trans for a deficiency in E4-ORF6 of an adenoviral genome.

19. The lung carcinoma cell of claim 16, wherein at least one non-adenoviral gene product is a viral protein.

20. The lung carcinoma cell of claim 16, wherein at least one non-adenoviral gene product is a cellular protein.

21. The lung carcinoma cell of claim 16, wherein the lung carcinoma cell is selected from the group consisting of an A549 cell, an NCI-H1299 cell, a Calu-1 cell, and an NC1-H460 cell.

22. The lung carcinoma cell of claim 16, wherein the lung carcinoma cell further comprises a heterologous nucleic acid sequence which upon expression produces a non-adenoviral gene product that enhances propagation of the replication-deficient adenoviral vector, so as to produce more replication-deficient adenoviral vectors when the heterologous nucleic acid sequence is present in the lung carcinoma cell than when it is absent from the lung carcinoma cell.

23. A method of propagating a replication-deficient adenoviral vector, which method comprises:
    (a) providing the lung carcinoma cell of claim 16,
    (b) introducing a replication-deficient adenoviral vector into the lung carcinoma cell, wherein the replication-deficient adenoviral vector comprises an adenoviral genome deficient in the at least one essential gene function of the E1 region and either or both of the E2A region and the E4 region, and
    (c) maintaining the lung carcinoma cell to propagate the replication-deficient adenoviral vector.

24. The lung carcinoma cell of claim 16, wherein the at least one heterologous nucleic acid sequence is integrated into the cellular genome.

25. The method of claim 23, wherein at least one non-adenoviral gene product complements in trans for a deficiency in the E1A region of an adenoviral genome.

26. The method of claim 23, wherein at least one non-adenoviral gene product complements in trans for a deficiency in E4-ORF6 of an adenoviral genome.

27. The method of claim 23, wherein at least one non-adenoviral gene product is a viral protein.

28. The method of claim 23, wherein at least one non-adenoviral gene product is a cellular protein.

29. The method of claim 23, wherein the lung carcinoma cell is selected from the group consisting of an A549 cell, an NCI-H1299 cell, a Calu-1 cell, and an NCI-H460 cell.

30. The method of claim 23, wherein the at least one heterologous nucleic acid sequence is integrated into the cellular genome.

31. A cell having a cellular genome comprising at least one heterologous nucleic acid sequence which upon expression produces at least one non-adenoviral gene product that complements in trans for a deficiency in at least one essential gene function of the E4 region of an adenoviral genome so as to propagate a replication-deficient adenoviral vector comprising an adenoviral genome deficient in the at least one essential gene function of the E4 region when present in the cell.

32. The cell of claim 31, wherein the cell further comprises a heterologous nucleic acid sequence which upon expression produces at least one non-adenoviral gene product that complements in trans for a deficiency in the E1A region of an adenoviral genome.

33. The cell of claim 31, wherein at least one non-adenoviral gene product complements in trans for a deficiency in E4-ORF6 of an adenoviral genome.

34. The cell of claim 31, wherein at least one non-adenoviral gene product is a viral protein.

35. The cell of claim 31, wherein at least one non-adenoviral gene product is a cellular protein.

36. The cell of claim 31, wherein the at least one heterologous nucleic acid sequence is integrated into the cellular genome.

37. A method of propagating a replication-deficient adenoviral vector, which method comprises:
    (a) providing the cell of claim 31,
    (b) introducing a replication-deficient adenoviral vector into the cell, wherein the replication-deficient adenoviral vector comprises an adenoviral genome deficient in the at least one essential gene function of the E4 region, and
    (c) maintaining the cell to propagate the replication-deficient adenoviral vector.

* * * * *